(12) United States Patent
Serfling et al.

(10) Patent No.: US 9,696,271 B2
(45) Date of Patent: Jul. 4, 2017

(54) SENSOR AND METHOD FOR MANUFACTURING THE SENSOR

(71) Applicant: Endress + Hauser Conducta Gesellschaft für Mess- und Regeltechnik mbH + Co. KG, Gerlingen (DE)

(72) Inventors: Alexander Serfling, Leipzig (DE); Stephan Buschnakowski, Chemnitz (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 66 days.

(21) Appl. No.: 14/950,913

(22) Filed: Nov. 24, 2015

(65) Prior Publication Data

US 2016/0153925 A1    Jun. 2, 2016

(30) Foreign Application Priority Data

Dec. 2, 2014    (DE) .................... 10 2014 117 685

(51) Int. Cl.
*G01N 27/02* (2006.01)
*G01R 27/08* (2006.01)
(Continued)

(52) U.S. Cl.
CPC ............. *G01N 27/07* (2013.01); *G01N 17/00* (2013.01); *G01N 27/06* (2013.01); *G01R 27/22* (2013.01);
(Continued)

(58) Field of Classification Search
CPC ........ G01N 27/00; G01N 27/02; G01N 27/04; G01N 27/06; G01N 27/07; G01N 17/00;
(Continued)

(56) References Cited

U.S. PATENT DOCUMENTS 3,736,548 A  *  5/1973  Double ................ H01R 13/523
                                                        174/74 R
4,128,469 A  *  12/1978  Rohr .................... G01N 27/407
                                                        204/427

(Continued)

FOREIGN PATENT DOCUMENTS

| DE | 19724309 A1 | 12/1998 |
| DE | 102007004895 A1 | 8/2008 |
| DE | 102007016477 A1 | 10/2008 |
| DE | 102008054659 A1 | 6/2010 |
| WO | 2008122467 A1 | 10/2008 |

OTHER PUBLICATIONS

German Search Report, German PTO, Munich, DE, Jan. 8, 2015.

*Primary Examiner* — Hoai-An D Nguyen
(74) *Attorney, Agent, or Firm* — Christopher R. Powers; PatServe

(57) ABSTRACT

A sensor, especially a conductive conductivity sensor, to determine a measurand, especially the conductivity, of a medium, including: a process interface shaped as a hollow cylinder and made of a metal, with the process interface having at least two internal segments; a mainly cylinder-shaped sensor element that is mainly made of a ceramic, with a first section to introduce the sensor element into the process interface and a second section with which the sensor element protrudes from the process interface. The first section of the sensor element has at least two segments, wherein the respective first segment of the process interface and the sensor element are designed as a press fit, and the respective second segment of the process interface and the sensor element create a gap and a method to manufacture such a sensor.

13 Claims, 3 Drawing Sheets

(51) Int. Cl.
*G01N 27/07* (2006.01)
*G01N 27/06* (2006.01)
*G01N 17/00* (2006.01)
*G01R 27/22* (2006.01)
*G01N 27/04* (2006.01)
*G01R 27/02* (2006.01)
*G01R 3/00* (2006.01)

(52) U.S. Cl.
CPC .............. *G01N 27/02* (2013.01); *G01N 27/04* (2013.01); *G01R 3/00* (2013.01); *G01R 27/02* (2013.01)

(58) Field of Classification Search
CPC ........ G01R 27/00; G01R 27/02; G01R 27/22; G01R 1/06788; G01R 1/07307; G01R 1/07342
USPC ....... 326/425, 439, 446, 600, 649, 691, 693, 326/694, 696, 715, 722, 724, 754.03, 326/755.01, 76.11, 149; 439/76.1, 166, 439/170, 174, 175, 283, 913
See application file for complete search history.

(56) References Cited

U.S. PATENT DOCUMENTS

| | | | |
|---|---|---|---|
| 5,854,557 A * | 12/1998 | Tiefnig | G01N 17/00 204/404 |
| 5,921,591 A * | 7/1999 | Argent | E21B 17/0426 228/135 |
| 6,112,592 A | 9/2000 | Kathan | |
| 6,206,432 B1 * | 3/2001 | Kamiyama | F16L 37/23 285/315 |
| 6,328,581 B1 * | 12/2001 | Lee | H01R 31/06 439/106 |
| 7,138,926 B2 * | 11/2006 | Henry | G01D 11/24 340/680 |
| 7,425,138 B2 | 9/2008 | Buhl | |
| 7,942,695 B1 * | 5/2011 | Lu | H01R 9/0524 439/578 |
| 9,000,784 B2 | 4/2015 | Eberheim | |
| 2007/0232147 A1 * | 10/2007 | Herberg | F16L 13/142 439/638 |
| 2013/0244506 A1 * | 9/2013 | Endo | H01R 4/48 439/825 |

* cited by examiner

SENSOR AND METHOD FOR MANUFACTURING THE SENSOR

TECHNICAL FIELD

The invention concerns a sensor, especially a conductive conductivity sensor to determine a measurand, especially the conductivity of a medium. The invention furthermore concerns a method to manufacture said sensor.

BACKGROUND DISCUSSION

A conductive conductivity sensor, e.g. from published International Application, WO 2010/072483, is known from the state of the art. The latter comprises at least two electrodes that are immersed into the medium to be measured for the measurement. In order to determine the electrolytic conductivity of the medium, one determines the resistance or conductance of the electrode measuring path in the medium. If the cell constant is known, this information then serves to detect the conductivity of the measuring medium. The electrodes are connected to a measuring transducer via a line or a cable. The latter then serves to determine the conductivity based on the measuring data.

The electrodes are embedded into a sensor element. The sensor element in turn is connected to a process interface. This combination of sensor element and process interface shall be referred to as "sensor" in the following. The process connection serves to connect the sensor to the medium to be measured. The process interface may, for example, be introduced into the medium via fittings, e.g. quick-change fittings.

At the connection point between sensor element and process interface, edges, ridges, burrs and other irregularities occur on the sensors at the current state of technology. Dirt, dust and medium may stick to such areas. Consequently, such a sensor is not suitable for hygienic requirements.

SUMMARY OF THE INVENTION

The invention addresses the task of supplying a sensor that meets hygienic requirements. In particular, the hygienic requirements pursuant to the FDA for direct food contact, USP Class VI; 3A and EHEDG are to be met.

This task is solved by a sensor with a process interface mainly shaped as a hollow cylinder and made of a metal, especially stainless steel, with the process interface having at least two internal segments; and a mainly cylinder-shaped sensor element that is mainly made of a ceramic, with a first area to introduce the sensor element into the process interface and a second area with which the sensor element protrudes from the process interface, wherein the first area of the sensor element has at least two segments, with the respective first segment of the process interface and the sensor element being designed as a press fit, and the respective second segment of the process interface and the sensor element creating a gap.

Consequently, the sensor element may be introduced into the process interface without edges, ridges, burrs, in general free of irregularities, to thus meet the standard hygiene requirements.

In one advantageous further development, the gap is designed to accept glue, and the sensor element is glued to the process interface. This strengthens the connection of the sensor element and the process interface.

In one preferred arrangement, the process interface has at least one internal cylindrical first and a second segment, with the first segment having a first inner radius and the second segment having a second inner radius. The second segment is arranged at one end section of the process interface and the second inner radius is larger than the first inner radius.

Advantageously, the first section of the sensor element features at least one cylindrical first segment and a cylindrical second segment, with the first segment having a first outer radius and the second segment at least one second outer radius, with the first outer radius of the sensor element mainly corresponding to the first inner radius of the process interface and being designed to be press-fit for the first segment of the sensor element and the first segment of the process interface.

It is preferred that the second segment of the sensor element and the second segment of the process interface create the gap. Due to the cylindrical form of the sensor element and the process interface, the gap extends axially with regard to the common cylinder axis.

In one preferred further development, the gap is designed as a groove in the second segment of the sensor element, wherein especially the second outer radius is smaller than the first radius. This is easy to manufacture and allows the reception of the glue.

In one advantageous arrangement, the process interface has partly at least a first outer radius and a second outer radius, wherein the process interface comprises the second outer radius in one end section and wherein the second outer radius is larger than the first outer radius. By grinding and/or turning (see below) of the larger outer radius onto the smaller outer radius, one may obtain a transition between the sensor element and the process interface that meets hygienic requirements.

In one advantageous embodiment, the sensor element comprises at least two, preferably four, metal electrodes, and the sensor element is designed in such a way that at least one front of the electrodes is in contact with the medium.

Advantageously, the electrodes are designed for measuring the measurand, especially conductivity, and connected to a data processing unit via the sensor element and the process interface. This allows the determination of a measurand using suitable measuring electronics.

The task is further solved by a process to manufacture a sensor, with the sensor comprising a process interface and a sensor element, including the steps of: manufacturing of a process interface that is mainly shaped as a hollow cylinder and made of metal, especially stainless steel, wherein the process interface has at least two interior segments; manufacturing of the mainly cylinder-shaped sensor element of a ceramic, with a first section to introduce the sensor element into the process interface and a second section that makes the sensor element protrude from the process interface, wherein the first section of the sensor element has at least two segments, with the respective first segment of the process interface and the sensor element being designed as a press fit, and the respective second segment of the process interface and the sensor element creating a gap; degreasing of the process interface and the sensor element; and joining the sensor element into the process interface by gluing, by introducing glue at least into the gap and introducing the sensor element into the process interface.

The method furthermore preferably includes the step of: thermal treatment of the sensor in an oven. The glue is dried thereby.

In one advantageous further development, the process interface at least in part features a first outer radius and a second outer radius, wherein the process interface comprises the second outer radius in one end section and wherein the second outer radius is larger than the first outer radius. The method preferably further includes the following step: grinding and/or turning of the end section of the process interface with the second outer radius, and grinding the second section of the sensor element onto the first outer radius of the process interface and/or polishing the end section of the process interface and the second section of the sensor element. By grinding and/or the larger outer radius onto the smaller outer radius, one may obtain a transition between the sensor element and the process interface that meets hygienic requirements. The transition is free of edges, gaps, ridges etc.

The sensor element preferably includes at least two current electrodes and two voltage electrodes, with an alternate current being applied between the current electrodes, wherein the potential difference created between the voltage electrodes is measured, especially by means of currentless measuring, wherein the alternate current applied and the potential difference measured are used to determine the measurand, especially the conductivity of the medium.

BRIEF DESCRIPTION OF THE DRAWINGS

The invention is further illustrated with reference to the following figures. They show.

DETAILED DISCUSSION IN CONJUNCTION WITH THE DRAWINGS

In the figures, the same features are characterized with the same reference symbols.

Figure 1:
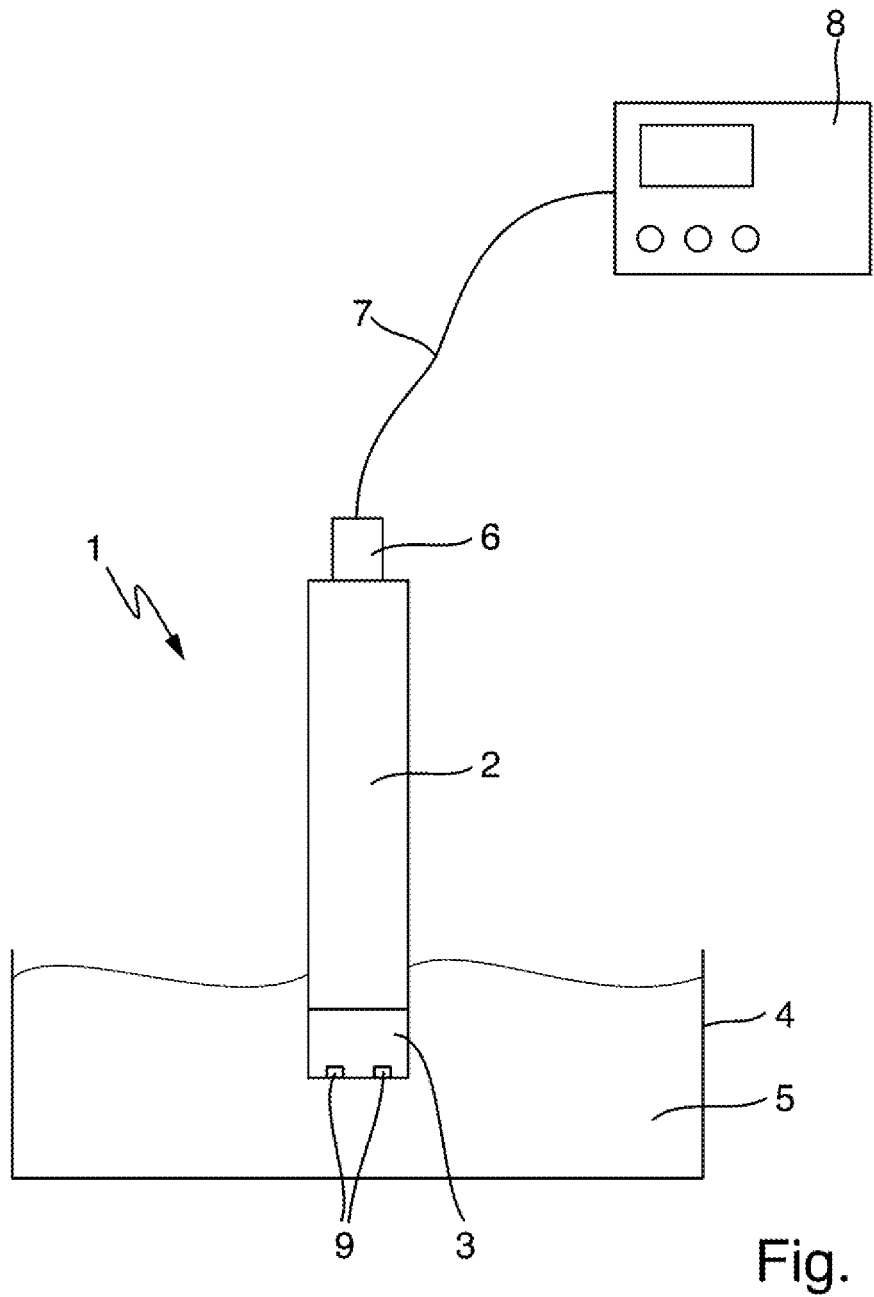
FIG. 1, an overview of a sensor according to the invention.

The sensor according to the invention in its entirety is marked with the reference symbol 1 and is shown in FIG. 1.

The invention shall be explained on the basis of a conductivity sensor, especially on the basis of a conductive conductivity sensor. The underlying idea may also be applied to other types of sensors using metal electrodes. A wide variety of sensors from the area of process automation such as pH sensors, amperometric sensors, etc. is conceivable.

The sensor 1 includes a sensor element 3 and a process interface 2. The sensor element 3 is made of a technical ceramic, such as zirconium dioxide, generally of a material that is not electrically conductive. In one embodiment, the zirconium dioxide is stabilized by magnesium, aluminum or iridium. The process interface 2 is made of a metal, especially of stainless steel. The process interface 2 may be used to attach the sensor 1 to the container 4.

Figure 2:
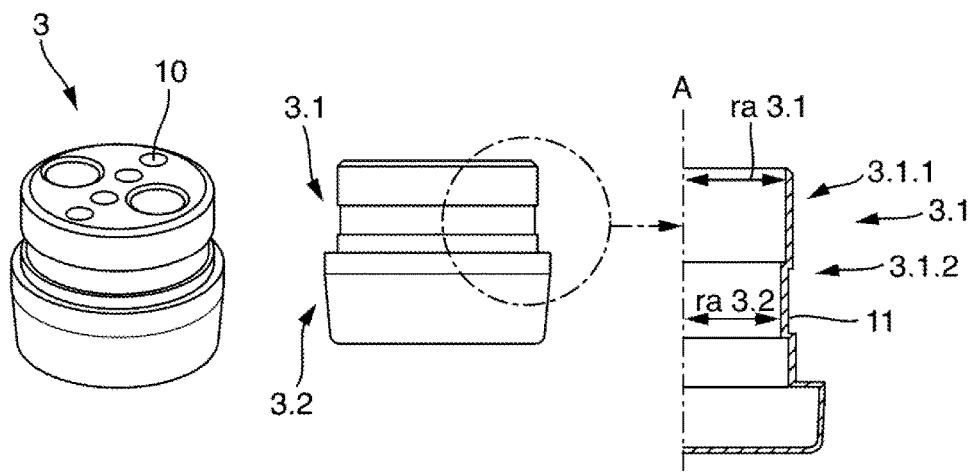
FIG. 2, one process interface of the sensor.

Metal electrodes 9, e.g. made of platinum, are embedded into the sensor element 3, more precisely in a recess (FIG. 2). The electrodes 9 and the sensor element 3 together form a composite material, i.e. they have, for example, been sintered together. This prevents any medium from penetrating into the interior of the sensor 1 between the electrodes 9 and the sensor element 3. On the front side of the sensor element 3, the front sides of the electrodes 9 are free and in contact with the medium 5 to be measured during a conductivity measurement. Preferably, the front sides of the electrodes 9 and the sensor element 3 are flush; however, the electrodes 9 may also protrude from the sensor element 3 in one embodiment, or be arranged more recessed on the sensor element 3.

FIG. 1 shows a sensor 1 that measures a medium 5 in a container 4. This container 4 may be a basin, pipe, line etc. A device (not shown) is used to attach the sensor 1 to the container 4, such as a bracket or a fitting, for example a quick-change fitting.

Basically, two embodiments of the conductive conductivity sensor are possible, namely with two or with four electrodes 9. FIG. 1 shows an arrangement with two electrodes 9.

During a measuring mode, an alternate current is applied to both electrodes 9. Impedance is determined by the sensor 1 immersed into the medium 5 using a measuring transducer 8 connected to the electrodes 9. The electrodes 9 are connected to an interface 6 with connecting terminals, e.g. cables via the sensor element 3 and the process interface 2 connected to the sensor element 3. An interface 6 or a cable that also includes an interface 6 connects the electrodes 9 with a measuring transducer 8. The interfaces 6 may be designed as galvanically separate, e.g. inductive interfaces.

Taking the cell constant of the sensor into account, the specific resistance and/or the specific conductivity of the medium 5 may be determined. The measuring data found may either be displayed by the measuring transducer 8 or be outputted to a higher-level control system. One part of the functions of the measuring transducer 9 may be executed by measuring electronics housed separately outside the measuring transducer 9. Such measuring electronics may, at least in part, for example be housed in the sensor 1, e.g. in the area of interface 6.

As an alternative to a 2-electrode sensor, a 4-electrode sensor is possible. The construction is basically the same. Two of the electrodes 9, especially two electrodes 9 in immediate vicinity, are operated as so-called current electrodes. The other two electrodes 9 are operated as so-called voltage electrodes. An alternate current is applied between the two current electrodes in measuring mode, and thus an alternate current is introduced into the measuring medium. The resulting potential difference is measured between the voltage electrodes, especially by means of currentless measuring. The alternate current applied and the potential difference measured may be used to calculate the impedance of the conductivity measuring cell created by immersing the sensor 1 into the medium 5, which then serves to determine the specific resistance and/or conductivity of the measuring medium, taking the cell constant into account. The measuring transducer 8 connected with the sensor 1 serves to adjust and/or control the alternate current to be introduced, to measure the potential difference of the voltage electrodes and to recalculate the measuring values as a resistance and/or conductivity value or a specific resistance and/or specific conductivity of the measuring media. As mentioned above, the link is effected e.g. via connections 6. The measuring electronics may be part of the measuring transducer 9 or be housed at least partially in a separate module, e.g. in sensor 1. The measuring data found may either be displayed by the measuring transducer 9 or be outputted to a higher-level control system. As an alternative to a measuring transducer 9, the measuring values may also be directly transmitted from sensor 1 to a bus; this constitutes a direct connection between the arrangement and the control system. Furthermore, an electronic system is required that conducts, for example, pre-processing of measuring data such as averaging, etc. as well as digitalization as well as transformation of the measuring data into the respective bus protocol.

FIG. 2 shows the sensor element 3. From left to right, the sensor element 3 is shown in 3-D view, as a section view as well as an enlargement of the section view.

The sensor element 3 comprises a first section 3.1 to introduce the sensor element 3 into the process interface 2 (see below) and a second section 3.2 which makes the sensor element 3 protrude from the process interface 2. The first section 3.1 is divided into at least two cylindrical segments, namely a first segment 3.1.1 and a second segment 3.1.2. The first segment 3.1.1 has a first outer radius ra3.1, the second segment 3.1.2 has a second outer radius ra3.2. Furthermore, the second section 3.2., i.e. the section of the sensor element 3 that protrudes from the process interface, has a third outer radius ra3.3. Consequently, the third outer radius ra3.3 is larger than the two other outer radii ra3.1 and ra3.2. In addition, the first outer radius ra3.1 is larger than the second outer radius ra3.2.

Figure 3:
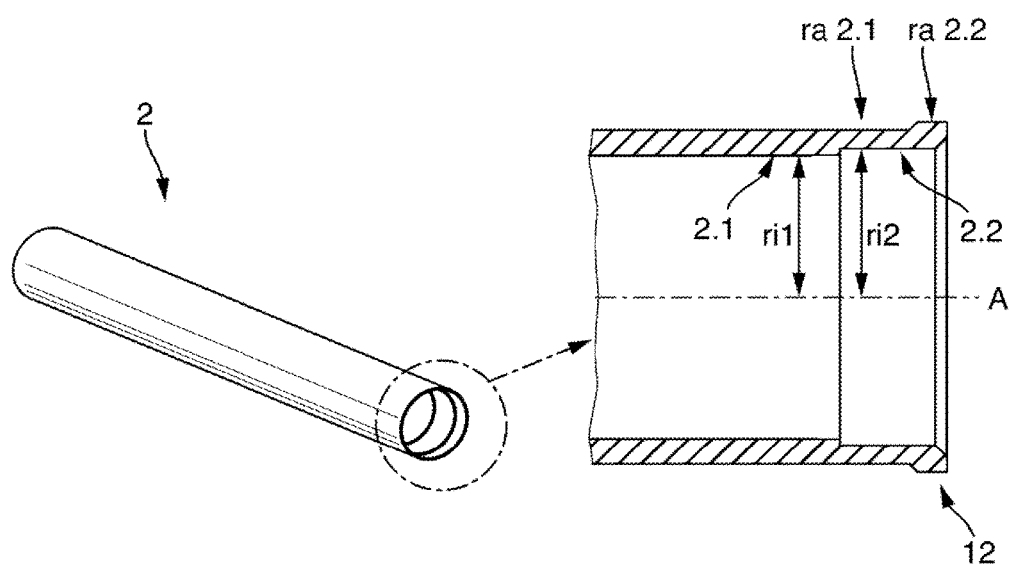
FIG. 3, one sensor element of the sensor.

FIG. 3 shows the process interface 2. From left to right, the process interface 2 is shown in a 3-D view and in section view.

The process interface 2 internally has at least two cylindrical segments 2.1 and 2.2, featuring the inner radii ri1 and/or ri2 respectively. The second inner radius ri2 is larger than the first inner radius ri1 and attached in an end section 12 of the process interface 2. The first inner radius ri1 mainly corresponds to the first outer radius ra2.1 of the sensor element 2.

If the sensor element 3 is introduced into the process interface 2, the first inner radius ri1 and the first outer radius ra2.1 form a press fit. The second segment 2.2. of the process interface 2 and the second segment 3.1.2 of the sensor element 3 form a gap. Preferably, the second segment 3.1.2 features a groove 11. This groove 11 is coated with glue before the sensor element 3 is brought into contact with the process interface 2. This creates a glue area to strengthen the connection as well as a tolerance area serving to center the sensor element 3.

Before applying the glue, the sensor element 3 is degreased with a solvent and then plasma-activated, e.g. under an argon-hydrogen mix (alternatively nitrogen).

The process interface 2 is also degreased. The gluing area is then roughened and silicatized. The gluing area then has to be cleaned and dried again. The glue is applied all around on the gluing area without bubbles, so as to wet the entire area.

When the sensor element 3 is press-fitted into the process interface, the glue is captured in the groove 11. Excess glue is pressed out of the gluing gap shortly before it is closed and can be wiped off.

The groove of, for example, 0.1 mm creates two segments sections with different glue "thickness". The thinner segment is ideal for the mechanical strength of the glue connection. The thicker segment is better suited to compensate the different expansion coefficients of stainless steel and ceramics at varying temperatures and thus helps to improve tightness.

The sensors are then dried and the glue hardened, e.g. in an oven.

Figure 4A:
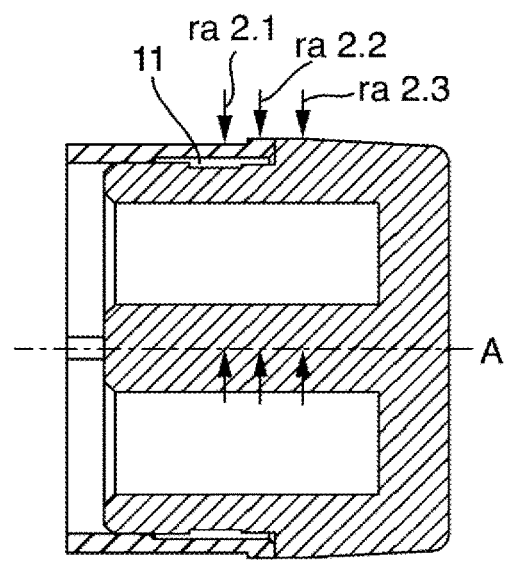
FIGS. 4a, 4b and 4c are section views of a sensor according to the invention, a lateral view before (FIG. 4b) and after (FIG. 4c) grinding of the end section of the process interface.
Figures 4B, 4C:
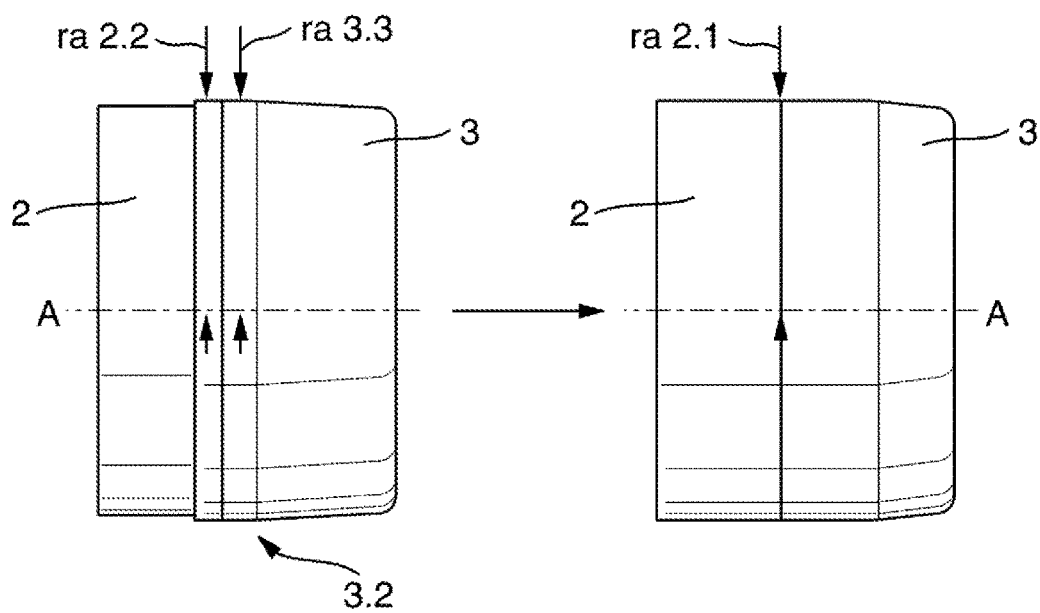

FIG. 4a and FIG. 4b show this bonded sensor 1 as a section view and a lateral view respectively. The process interface 2 in part features a first outer radius ra2.1 and a second outer radius ra2.2, wherein the process interface 2 comprises the second outer radius ra2.2. in one end section 12 and wherein the second outer radius ra2.2 is larger than the first outer radius ra2.1. In another manufacturing step, this end section 12 of the process interface 2 is adjusted to the second outer radius ra2.2. as well as the second section 3.2 of the sensor element 3 by cylindrical grinding on the first outer radius ra2.1 of the process interface 2, see also FIG. 4c. Alternative or in addition, these areas may be polished, e.g. using diamond paste. This creates a stepless transition, with the roughness not exceeding an average roughness of $R_a$=0.76 even in the transition area.

This means that the sensor 1 complies with standard hygienic requirements such as those in the standards pursuant to FDA, USP Class VI; 3A and EHEDG.

The invention claimed is:

1. A sensor to determine the conductivity of a medium, comprising:
    a process interface shaped mainly as a hollow cylinder and made of metal, said process interface comprises at least two internal segments; and
    a mainly cylinder-shaped sensor element that is mainly made of a ceramic, with a first section to introduce said sensor element into said process interface and a second section with said sensor element protrudes from said process interface, wherein:
    said first section of the sensor element has at least two segments; and
    said respective first segment of said process interface and said sensor element being designed as a press fit, and the respective second segment of said process interface and said sensor element creating a gap.

2. The sensor according to claim 1, wherein:
    said gap is designed to accept glue and said sensor element being glued to said process interface.

3. The sensor according to claim 1, wherein:
    said process interface has at least one internal cylindrical first and a cylindrical second segment, with said first segment having a first inner radius and said second segment having a second inner radius;
    said second segment is arranged at one end section of said process interface and said second inner radius being larger than said first inner radius.

4. The sensor according to claim 3, wherein:
    said first section of said sensor element has at least one cylindrical first segment and a cylindrical second segment;
    said first segment has a first outer radius and said second segment has at least a second outer radius; and
    said first outer radius of said sensor element mainly corresponds to said first inner radius of said process interface and is designed for a press-fit of said first segment of said sensor element and said first segment of said process interface.

5. The sensor according to claim 4, wherein:
    said second segment of said sensor element and said second segment of said process interface create said gap.

6. The sensor according to claim 5, wherein:
    said gap is designed as a groove on said second segment of said sensor element; and
    said second outer radius is smaller than said first outer radius.

7. The sensor according to claim 3, wherein:
    said process interface in part features at least a first outer radius and a second outer radius;
    said process interface at one end section comprises said second outer radius; and
    said second outer radius is larger than said first outer radius.

8. The sensor according to claim 3, wherein:
said sensor element comprises at least two, preferably four metal electrodes; and
said sensor element is designed in such a way that at least the front side of said electrodes is in contact with the medium.

9. The sensor according to claim 8, further comprising:
a data processing unit, wherein:
said electrodes are designed to measure the measurand, especially conductivity, and are connected to said data processing unit by means of said sensor element and said process interface.

10. A method for manufacturing a sensor, to determine the conductivity of a medium, wherein the sensor comprising a process interface and a sensor element, the method comprising the steps of:
manufacture of the process interface shaped mainly as a hollow cylinder of metal, the process interface comprises at least two internal segments;
manufacture of the mainly cylinder-shaped sensor element of a ceramic, with a first section to introduce the sensor element into the process interface and a second section with which the sensor element protrudes from the process interface, the first section of the sensor element has at least two segments, and with a respective first segment of the process interface and a sensor element being designed as a press fit, and the respective second segment of the process interface and the sensor element creating a gap;
degreasing of the process interface and the sensor element; and
press-fitting the sensor element into the process interface by gluing, by introducing glue at least into the gap and inserting the sensor element into the process interface.

11. The method according to claim 10, further comprising the step of:
thermal treatment of the sensor in an oven.

12. The method according to claim 11, wherein:
the process interface is mainly shaped as a hollow cylinder in part featuring at least a first outer radius and a second outer radius;
the process interface at one end section comprises the second outer radius and said second outer radius is larger than the first outer radius, and
with the method further comprising the step of:
grinding and/or turning of the end section of the process interface with the second outer radius, and grinding the second section of the sensor element onto the first outer radius of the process interface and/or polishing the end section of the process interface and the second section of the sensor element.

13. The method according to claim 10, wherein:
the sensor element includes at least two current electrodes and two voltage electrodes;
an alternate current is applied between the current electrodes;
the potential difference created between the voltage electrodes is measured, by means of currentless measuring; and
the alternate current applied and the potential difference measured are used to determine the measurand, especially the conductivity of the medium.

* * * * *